United States Patent [19]

Satzinger et al.

[11] Patent Number: 4,724,266
[45] Date of Patent: Feb. 9, 1988

[54] PHARMACEUTICAL COMPOSITION WITH ANTITHROMBOTIC ACTIVITY

[75] Inventors: Gerhard Satzinger, Denzlingen; Günter Wolf, Freiburg; Hartmut Osswald, Waldkirch; Ute Weiershausen, Gundelfingen, all of Fed. Rep. of Germany

[73] Assignee: Godecke Aktiengesellschaft, Berlin, Fed. Rep. of Germany

[21] Appl. No.: 76,240

[22] Filed: Jul. 21, 1987

[30] Foreign Application Priority Data

Jul. 31, 1986 [DE] Fed. Rep. of Germany ....... 3626097

[51] Int. Cl.⁴ .............................................. C07C 69/00
[52] U.S. Cl. .................................... 560/143; 540/488; 514/211; 514/546
[58] Field of Search ......................... 560/143; 540/488

[56] References Cited

U.S. PATENT DOCUMENTS 4,590,188  5/1986  Takeda et al. ...................... 540/488

FOREIGN PATENT DOCUMENTS

62/29525  2/1987  Japan .

Primary Examiner—Paul J. Killos
Attorney, Agent, or Firm—Elizabeth M. Anderson

[57] ABSTRACT

The present invention provides combination of materials for strengthening the antithrombotic action of acetylsalicylic acid. It covers a composition which contains diltiazem or a pharmaceutically acceptable acid-addition salt thereof in combination with acetylsalicylic acid. It also forms the new compound diltiazem acetysalicylate. It also covers compositions containing the above and methods for using the compositions or compound.

4 Claims, No Drawings

PHARMACEUTICAL COMPOSITION WITH ANTITHROMBOTIC ACTIVITY

BACKGROUND OF THE INVENTION

The antithrombotic action of the acetylsalicylic acid is known (Med. Klin., 76, 692/1981) but the optimum dosage is still open to debate. Recommendations vary between 300 mg/day and 3×500 mg/day or 4×325 mg/day. Acetylsalicylic acid brings about an irreversible inhibition of cyclooxygenase, an enzyme which produces thromboxane $A_2$ ($TXA_2$) in the thrombocytes. Without $TXA_2$, no arrest of hemorrhage, as desired effect, takes place and no aggregation of the blood platelets which is necessary for thrombogenesis. At the same time, however, acetylsalicylic acid also inhibits the cyclooxygenase of the intima of the blood vessels so that the endogenic aggregation inhibitor epoprostenol, $PGI_2$, cannot be formed. In this way, acetylsalicylic acid obtains a thrombogenic potency. Since the cyclooxygenase of the thrombocytes is more sensitive towards acetylsalicylic acid and is more slowly regenerated as that of the inner blood vessel walls, it is assumed that a certain differentiation of the acetylsalicylic acid effect can be achieved via the dosage.

On the one hand, because of the reduction of the acetylsalicylic acid side effects, which can be considerable and manifest themselves, especially in the gastrointestinal tract and in the kidneys, and, on the other hand, for the above-mentioned reasons, it is of decisive therapeutic importance to keep the dosage of the acetylsalicylic acid as low as possible. For the purposes of the present invention, this is achieved by a combination of acetylsalicylic acid with diltiazem.

SUMMARY OF THE INVENTION

The present invention is concerned with a combination of two effective substances which exhibit synergistic action; thereby strengthening the antithrombotic action of acetylsalicylic acid.

A rational prophylaxis and therapy must be oriented to the pathogenesis of the disease in question. In the case of diseases of the blood vessels involving occlusion, the thrombocytes are of decisive importance. This applies to the initial thrombogenesis in the arterial system as well as to the formation of coagulation thrombi in the venous circulation. Recent experimental knowledge also indicates that arteriopathies in the widest sense are to be regarded as being the result of a disturbed relationship between the walls of the blood vessels, that is the endothelium, and the thrombocytes. This knowledge provides new assumptions for appropriate causal therapeutic measures.

Since the in vivo thrombocyte aggregation is, in all probability, the result of simultaneous activation or production of several aggregationic factors, such as platelet-activating factor (PAF), adrenaline, ADP/ATP and lipoxygenase and cyclooxygenase products of arachidonic acid an extensive therapeutic effect cannot be expected from the action of a cyclooxygenase inhibitor, such as acetylsalicylic acid or sulfinpyrazone, alone.

Consequently, it is an object of the present invention to provide a new composition for the therapy and prophylaxis of thromboembolic diseases.

One aspect of the present invention is a new compound, diltiazem acetylsalicylate. Another aspect is a new pharmaceutical composition comprising from more than 60 to about 180 mg of diltiazem or a pharmaceutically acceptable acid addition salt thereof with from about 10 to 300 mg acetylsalicylic acid.

Still another aspect is a thrombolitically-effective pharmaceutical composition comprising an effective amount of the above composition together with a pharmaceutically acceptable carrier.

Yet another aspect is a method of treating or preventing thromboembolic diseases in mammals which comprises administering to said mammal the above pharmaceutical composition in unit dosage form.

DETAILED DESCRIPTION

Thus, according to the present invention, there is provided a synergistic combination of materials for strengthening the antithrombic action of acetylsalicyclic acid, wherein it contains diltiazem or a pharmaceutically acceptable acid-addition salt thereof in combination with acetylsalicylic acid.

Thromboembolic diseases are understood to include such diseases as: peripheral arterial and venous occlusive diseases/arteriopathies, prevention of thromboembolic complications; coronary heart disease, prophylaxis after heart infarct prevention of venous thromboses and arterial embolisms; cerebrovascular blood vessel diseases, ischaemias, insultus as a result of thromboembolic incidents; arteriosclerosis, reduction of risk factors; migraine, prophylaxis and therapy; and Raynaud syndrome, prophylaxis and therapy in the case of thromboembolic disposition.

It is surprising that diltiazem, a known coronary vasodilatory, even in combination with extraordinarily low dosages of acetylsalicylic acid, strengthens its therapeutic, thrombocyte aggregation-inhibiting action in a synergistic manner. A weakly inherent action of diltiazem inhibiting the aggregation of the blood platelets would be explicable since the activation of the phospholipase $A_2$ of the thrombocytes, the activation of the actomyosin of the platelets, and possibly also the platelet-derived growth factors (PDG) on the intima are under the control of calcium ions. However, it was not to have been foreseen that the combination of subtherapeutic dosages of diltiazem and acetylsalicylic acid would exercise a strong antiaggregating effect. Thus, because of the increased safety and effectiveness, the combination according to the present invention represents a real therapeutic advance.

A preferred dosage unit comprises 60 to 180 mg diltiazem or an acid addition salt thereof in combination with 10 to 300 mg acetylsalicylic acid and possibly also conventional adjuvants and carrier materials.

A more preferred dosage unit comprises 80 to 100 mg diltiazem or an acid addition salt thereof in combination with 50 to 100 mg of acetylsalicylic acid and possibly also conventional adjuvants and carrier materials.

As salts of diltiazem, there can be used the usual ones with organic and inorganic acids. The salts are usually obtained by neutralizing the base with appropriate inorganic or organic acids. As acids, there can be used, for example, hydrochloric acid, sulphuric acid, phosphoric acid, hydrobromic acid, acetic acid, tartaric acid, lactic acid, citric acid, malic acid, salicylic acid, ascorbic acid, malonic acid, and succinic acid.

Since diltiazem is basic by nature, the acetylsalicylic acid can also act directly as a salt former, especially because this salt contains the active materials in a very good relationship. One-hundred thirty mg of the new diltiazem acetylsalicylate contain about 90 mg of diltiazem active material and 40 mg of acetylsalicylic acid active material. A dosage unit of 65 mg of this salt contains about 45 mg diltiazem and 20 mg of acetylsalicylic acid. Thus, a composition with 100 mg diltiazem acetylsalicylate contains, per dosage unit, 30,3 mg acetylsalicylic acid and 69.7 mg diltiazem, which corresponds to a weight ratio of 1:2.3.

Diltiazem, or an acid-addition salt thereof, and acetylsalicylic acid, as well as diltiazem acetylsalicylate, can be employed in conventional compositions and in admixture with conventional pharmaceutically acceptable carriers and diluents.

The compositions according to the present invention can be administered orally or parenterally in liquid or solid form. As injection solution, water is preferably used which contains the additives usual in the case of injection solutions, such as stabilizing agents, solubilizing agents, or buffers.

The compositions can be present as conventional galenical formulations, such as tablets or capsules.

Additives of this kind include, for example, tartrate and citrate buffers; ethanol; complex formers, such as ethylenediamine-tetraacetic acid and the nontoxic salts thereof, as well as high molecular weight polymers, such as liquid polyethylene oxide, for viscosity regulation. Solid carrier materials include, for example, starch; lactose; mannitol; methyl cellulose; talc; highly dispersed silicic acid; high molecular weight fatty acids, such as stearic acid; gelatine; agar-agar; calciumphosphate; magnesium stearate; animal and vegetable fats; and solid high molecular weight polymers, such as polyethylene glycol. Compositions suitable for oral administration can, if desired, contain additional flavoring and/or sweetening agents.

The individual dosages of the new compositions are in the range of from 50 to 400 mg in the case of enteral administration and from about 5 to 50 mg in the case of parenteral administration.

Because of the known stability problems with solutions of acetylsalicylic acid, as parenteral preparations lyophilisates are especially preferred, which are first brought into solution shortly before use.

The present invention is explained in more detail on the basis of the following comparative experiments.

COLLAGEN-INDUCED THROMBOCYTE AGGREGATION MATERIALS AND METHODS

The experimental animals used were male Sprague-Dawley SIV 50 rats with a body weight of 200 g. The test substances were dissolved in water and administered to the animals twice daily by means of a stomach tube. The first administration took place at 3:00 PM on the preceding day and the second administration at 8:00 AM of the experimental day. After the first administration, food was removed from the animals but they still received water. Per administration, the animals received, in a volume of 1 ml/200 g body weight, the following dosages:

| | |
|---|---|
| placebo | only water |
| 1st dosage | 30 mg diltiazem/kg |
| 2nd dosage | 100 mg diltiazem/kg |
| 3rd dosage | 5 mg acetylsalicylic acid/kg |
| 4th dosage | 30 mg diltiazem/kg and 5 mg acetylsalicylic acid/kg |

At 9:00 AM on the experimental day, i.e., one hour after the second administration, blood was taken from the retroorbital venous plexus of the animals under ether narcosis. Nine parts of blood were mixed with one part of 3.8% (w/v) trisodium citrate solution. After lowspeed centrifuging of the mixture at ambient temperature, the platelet-rich plasma (PRP), corresponding to the erythrocyte-free supernatant, was removed and adjusted to a standard concentration of 400,000 μl. The aggregation test was carried out according to the method of Born (Nature, 194, 927–929/1962). The measurement instrument used was a universal aggregometer (Braun, Melsungen) connected with an Eppendorf photometer 1100M (Netheler & Hinz, Hamburg).

In the experiment, in each case 800 μl PRP were equilibrated in the aggregometer for three minutes at 37° C. and then, by the addition of 35 μl collagen suspension (collagen reagent HORM, Hormon Chemi, Munchen), the aggregation was initiated. A compensation recorder registered the change of transmission in the following five minutes. With increasing aggregation, in this test the transmission increases and the extinction decreases. The changes registered five minutes after addition of the collagen were evaluated and are set out in the following Table 1. The values are given as percentages, the extinction difference between PRP and platelet-free plasma serving as 100% value. The aggregation values obtained are set out in Table 1 below.

TABLE 1

| Test | Composition | Aggregation $\bar{x} \pm$ S.D. |
|---|---|---|
| | Placebo | 65 ± 12 |
| 1 | 30 mg/kg diltiazem | 63 ± 10 |
| 2 | 100 mg/kg diltiazem | 58 ± 10 |
| 3 | 5 mg/kg acetylsalicylic acid | 37 ± 12 |
| 4 | 30 mg/kg diltiazem and 5 mg/kg acetylsalicylic acid | 19 ± 15 |

$\bar{x} \pm$ S.D. in each case from six individual experiments.

From the above Table 1, it can be seen that dosage 4 results in a surprisingly low aggregation value.

EXAMPLE

Diltiazem-acetylsalicylate

A solution of 731,4 mg (1,76 m mol) diltiazem and 317,9 mg (1,76 m mol) acetylsalicylic acid is prepared in 10 ml water. The solution obtained is evaporated to dryness. The amorphous colourless residue is pulverized to a white powder.

Yield: 1000 mg.

The salt exhibits in the NMR-spectrum (solution in $CDCl_3$) the typical chemical shift expected for a salt, which is demonstrated in the following Table II:

TABLE II

Coordination and comparison of the NMR-signals of the diltiazem - acetylsalicylate - salt.

| Fragment | Chemical Shift δ in ppm | | $|\Delta\delta|$ | Multiplicity |
|---|---|---|---|---|
| | BASE | SALT | | |
| O‖C—CH$_3$ | 1,90 | 1,90 | — | S |
| N(CH$_3$)$_2$ | 2,27 | 2,60 | 0,33 | S |
| N—CH$_2$ | 2,46 | 2,94 | 0,48 | M |
| | 2,69 | 3,15 | 0,46 | M |
| O—CH$_3$ | 3,82 | 3,82 | — | S |
| N—CH$_2$ | 3,71 | 4,08 | 0,37 | M |
| | 4,42 | 4,46 | 0,04 | M |

TABLE II-continued

Coordination and comparison of the NMR-signals of the diltiazem - acetylsalicylate - salt.

| Fragment | Chemical Shift δ in ppm BASE | SALT | \|Δδ\| | Multiplicity |
|---|---|---|---|---|
| C—H | 5,01 | 5,01 | — | D |
| C—H | 5,16 | 5,13 | 0,03 | D |
| p-Methoxy-aromatic res. | | | | |
| m. =CH— | 6,89 | 6,90 | 0,01 | D |
| o. =CH— | 7,44 | 7.39 | 0,05 | D |
| Basic aromat. | 7,26 | 7,25 | 0.01 | M |
| H residue | 7,48 | 7,5 | , | M |
|  | 7,48 | 7,5 | , | M |
|  | 7,69 | 7,68 | 0,01 | DM |
| Acetylsalicylic acid | | | | |
|  | | 2,25 | | S |
| arom. =CH— | | 7.04 | | DD |
|  | | 7,25 | | M |
|  | | 7,5 | | M |
|  | | 7,96 | | DD |

We claim:

1. A compound having the name dilatiazem acetylsalicylate.

2. A pharmaceutical composition comprising from >60 to 180 mg diltiazem or a pharmaceutically acceptable acid addition salt thereof with from about 10 to 300 mg acetylsalicylic acid.

3. A thrombolitically-effective pharmaceutical composition comprising an effective amount of a compound according to claim 1 or a composition according to claim 2 together with a pharmaceutically acceptable carrier.

4. A method of treating or preventing thromboembolic diseases in mammals which comprises administering to said mammal a pharmaceutical composition according to claim 3 in unit dosage form.

* * * * *